United States Patent [19]

Parask

[11] Patent Number: 5,015,181

[45] Date of Patent: May 14, 1991

[54] HEATER FOR DENTAL IMPRESSION COMPOUND

[76] Inventor: Dale B. Parask, 3239 S. 58th St., Unit 307, Milwaukee, Wis. 53219

[21] Appl. No.: 248,637

[22] Filed: Sep. 26, 1988

[51] Int. Cl.$^5$ .............................................. A61C 19/00
[52] U.S. Cl. ...................................................... 433/32
[58] Field of Search .................... 433/32; 219/432, 433

[56] References Cited

U.S. PATENT DOCUMENTS 2,269,874  1/1942  Henschel ................................ 433/32
2,749,426  6/1956  Schwaneke ......................... 219/432
3,725,641  4/1973  Tilp ..................................... 219/433

*Primary Examiner*—Cary E. Stone
*Attorney, Agent, or Firm*—Fuller, Ryan & Hohenfeldt

[57] ABSTRACT

A heater for dental impression compound includes an insulative holder made of two hinged Teflon leaves which hold a metal container against an electrically heated plate to elevate the temperature of the compound to a working temperature. The holder enables manual handling of the heated container.

18 Claims, 1 Drawing Sheet

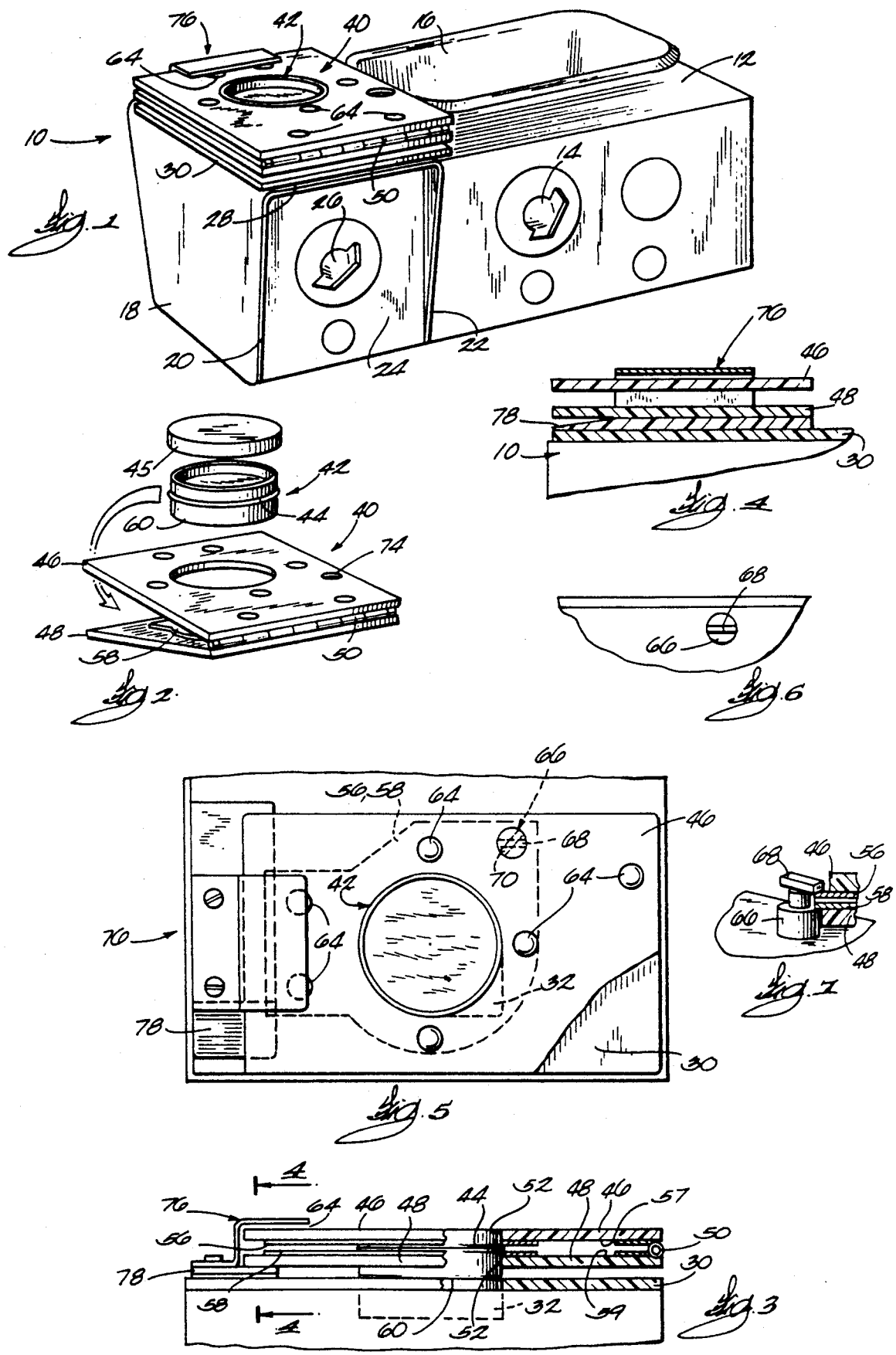

HEATER FOR DENTAL IMPRESSION COMPOUND

BACKGROUND OF THE INVENTION

The invention relates to method and apparatus for preparing a dental impression compound for use. It is particularly adapted for using the dental impression composition disclosed in U.S. Pat. No. 4,033,774, the entire patent of which is incorporated herein by reference. The product disclosed in that patent has been marketed under the trademark Zonarex which is a trademark for Zonarex Corporation. The impression compound is a thermal plastic material which must be heated to a working temperature for application to the tray. Dentists have used the Zonarex impression compound by heating a metal container in which the compound is sold with a tripod and an alcohol lamp. The dentists would manually manipulate the lamp to control the heat and thus the viscosity of the compound. An upper or lower jaw impression tray is then loaded with the impression compound to make the actual impression. The heated container is difficult and inconvenient to handle and manipulate. The use of alcohol lamps and tripods also involves some hazards.

SUMMARY OF THE INVENTION

The invention provides apparatus for precise, constant or variable temperature heating and manipulating of the impression compound containers to afford accurate, clean, safe and convenient use of the impression compound. The invention provides holder means for the containers with coaxial apertures in hinged upper and lower leaves or members which receive and support the container. The container has an annular projecting rib on the cylindrical side wall. This rib is sandwiched between the upper and lower leaves to hold the container in a positive position in the holder apertures.

A heater is provided to cooperate with the holder. The heater has a smooth heat transfer plate for conducting heat to the bottom of the impression compound container. A clamping bracket adjacent the transfer plate engages the holder and provides clamping pressure to press the container bottom against the heat transfer plate. In addition, control of the holder is provided by a locating pivot post on the top of the heater. The post is pivotally connected to an aperture in the holder to afford swinging movement of the holder into contact with the clamping bracket and to secure the holder in the full heating position or a partial heating position.

Metal plates are fixed to the inside of the holder leaves to add weight to the holder and thus, add to clamping pressure of the container bottom against the heat transfer plate. Co-axial apertures in the plates provide aperture walls in heat transfer contact with the side wall of the container. The heavy plates act as a heat sink to maintain relatively constant temperature of the container during use. The plates also add rigidity to the heated Teflon plates. The upper and lower members also are desirably made of Teflon which is easy to clean and which provides an insulative handling surface for manual carrying of the holder to the sink for cooling and discarding of the hot container. The heat transfer surface on the heater is surrounded by a Teflon plate to aid in easy cleaning. The heater is desirably associated with a thermostatically controlled hot water bath to enable immersion of the filled impression tray in a bath maintained at a selected temperature to ensure that the compound in the tray is at a temperature which is at a safe level for the patient and appropriate temperature for accurate impressions.

The container is sized to provide sufficient compound for a single patient either an upper or lower impression.

Further objects, features and advantages of the invention will become apparent from the disclosure.

DESCRIPTION OF THE DRAWINGS

FIG. 1 is a perspective view of the heater and impression compound holder of the invention;

FIG. 2 is a perspective view of the holder and container;

FIG. 3 is a side elevational view in fragmentary section of the apparatus shown in FIGS. 1 and 5;

FIG. 4 is a sectional view along line 4—4 of FIG. 3;

FIG. 5 is a plan view of the apparatus shown in FIG. 1;

FIG. 6 is a top view of the locating post and a fragment of the holder; and

FIG. 7 is a perspective view of the locating post.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings FIG. 1 illustrates a heater 10 in accordance with the invention. The heater 10 is coupled to a conventional water bath housing 12 which has a heater with a thermostatic control 14 to heat a water reservoir 16. The water bath housing adds stability to the heater 10.

The heater 10 has a housing 18 with side walls 20 and 22, and a panel 24 containing a dial 26 for a thermostatically controlled switch for a heater, not shown. The housing is provided with a top wall 28 which is provided with a Teflon top plate 30. An aperture in the Teflon top plate 30 exposes a heat transfer plate 32 which extends through the aperture and is flush with the surface of plate 30. The heat transfer plate 32 is in contact with an electrical heating element, not shown.

As shown in FIG. 2, a holder 40 is provided for manipulating a thin metal container 42 which contains a sufficient quantity of impression compound for an upper or lower impression. The container is a throw-away container and a small size would contain 28.4 grams. The container 42 has an annular protruding rib 44 which spans the circumference of the container. The container 42 is also provided with a cap 45 which is removed when the container is inserted in the holder.

The holder is provided with upper and lower leaves or members 46 and 48 which are hinged together by a hinge 50. The members 46 and 48 are provided with coaxial apertures 52 which are sized to snugly receive the side wall of the container 42. The apertures 52 have a diameter less than the diameter of the rib 44. Thus when the rib is located between the leaves as shown in FIG. 4, the leaves snugly secure the container in the holder with the rib preventing the container from moving in or out with respect to the apertures 52. The leaves 46 and 48 are desirably constructed of Teflon which are easy to clean and which provide an insulating surface for manual manipulation. The upper leaf 46 serves as an apron which fits tightly around the can to prevent water or compound from reaching heating plate 32. The Teflon top plate 30 is in a tight fit with plate 32 to prevent water and compound from reaching the heating element not shown. The holder is provided with metal plates 56 and 58 on the inside surfaces 57, 59 of the leaves to provide extra weight to the leaves to hold the container bottom 60 in contact with the heat transfer plate 32. The metal plates 56 and 58 also add rigidity to the Teflon leaves. The plates are secured to the leaves by rivets 64 which protrude above and below the Teflon surface.

Means are provided for securing the holder in heat transfer contact with the heat transfer plate. In the disclosed construction the means includes a pivot post 66 provided with a key 68 which interfits in the corresponding aperture or key hole 70 in the holder which extends through the lower Teflon plate and the upper and, lower metal plates. A window or opening 74 in leaf 46 enables the user to visually position the holder on the key 68. The key permits insertion of the holder in only one position when the key and keyway are aligned. When the holder is pivoted into the FIG. 1 position, the key prevents accidental displacement of the holder from the heater during the heating period. The pivot post enables the user to position the holder at any angular position relative to the heat transfer plate to control the viscosity and heating rate with full or partial contact of the container with the plate 32. The pivot post will thus retain the holder on the heater although not clamped in the FIG. 1 position.

Clamping means are also provided to secure the holder in heat transfer contact in the FIG. 1 position. In the disclosed construction the means includes a bracket 76 which has an upper portion which is positioned over the Teflon plates when the holder is in the FIG. 1 heating position. A ramp 78 made of Teflon provides a lead-in to urge the holders into the gap between the clamping plate and a Teflon plate in opposed relation to secure the holder in place. Rivets 64 engage the bracket 76 as shown in FIG. 1.

In use it takes approximately three minutes to heat a container to an appropriate temperature for applying to the impression tray. Water bath temperature is also set at a selected temperature, such as 160°. After heating the container with the heater assembly, the impression compound is removed from the container applied to the tray which then is immersed in the water bath to provide a temperature for an accurate impression. At all times during use the container will be contained between the leaves of the holder which facilitates manipulation of the container 42 to control the temperature for the best viscosity for applying the tray.

The thermostatically controlled heater enables maintaining the compound at a certain temperature for an extended period of time. This was not possible with the alcohol lamp set up previously used.

Use of the sized container for one patient prevents cross-contamination. The holder can also be sterilized.

I claim:

1. The combination of heating apparatus and a dental impression compound said combination comprising:
   a container containing said compound and having a side wall connected to a heat conductive bottom said side wall having a projecting rib;
   a heater having a heater plate; and
   holder means for manipulating said container, said holder means cooperating with said side wall rib to hold said container and heat conductive bottom in heat transfer contact with said heater plate to heat said dental impression compound and means for pressing said holder means and container in contact with said heater plate.

2. Apparatus in accordance with claim 1 wherein said holder means comprises a pair of opposed members and hinge means hingedly connecting said members, said members having coaxial apertures sized to receive said container with said opposed members having an aperture diameter less than the diameter of said rib to support the container with the rib located between said opposed members.

3. Apparatus in accordance with claim 2 wherein said pressing means for pressing said holder means comprises weights on said opposed members to firmly press the container against said heater plate.

4. Apparatus in accordance with claim 2 wherein said weights have coaxial apertures with said apertures in said members.

5. Apparatus in accordance with claim 2 wherein said upper and lower members are made of Teflon and sized to enable manual carrying of the assembly for quick cooling and storing.

6. Apparatus in accordance with claim 2 wherein said upper member provides an apron surrounding the open can to prevent compound and water from entering the heater area.

7. Apparatus in accordance with claim 2 wherein said heater plate is surrounded by a tight fitting Teflon plate to seal the heater against water and compound.

8. Apparatus in accordance with claim 1 wherein said means for pressing said holder means comprises a ramp on the surface of said heater and a bracket on said heater surface in opposed relation to said ramp, said opposed members being received between said bracket and said ramp under clamping pressure to hold said container in heat transfer contact with said heater plate.

9. The apparatus of claim 1 wherein said container is sized to hold sufficient dental impression compound for a large maxillary tray.

10. Apparatus in accordance with claim 1 including a pivot post on said heater and a cooperating aperture on said holder means to afford movement of the holder into and from a full heating position.

11. Apparatus in accordance with claim 1 wherein said heater is integrally connected to a heated water bath.

12. Apparatus for handling a dental impression compound comprising:
    a container having a side wall connected to a heat conductive bottom, said side wall having a projecting rib cooperating with a holder means for holding said container;
    said holder means comprising a pair of opposed members and hinge means hingedly connecting said members, said members having coaxial apertures sized to receive said container with said opposed members having an aperture diameter less than the diameter of said rib to support the container with the rib located between said opposed members;
    a heater having a heat-conductive plate; and
    said holder means holding said heat conductive bottom of said container in heat transfer contact with said heater to heat the contents of said container.

13. An apparatus for heating dental impression compound in a container, said container having a generally cylindrical side wall connected to a heat conductive bottom, said side wall having a rib projecting radially outward about substantially the entire circumference of said container, said apparatus comprising:

a heater having a heater plate; and holder means for manipulating said container, said holder means cooperating with said side wall rib to hold said heat conductive bottom of said container in heat transfer contact with said heater plate to heat said dental impression compound including pressing means for pressing said holder means and said container in contact with said heater plate.

14. Apparatus in accordance with claim 13 wherein said holder means comprises a pair of opposed leaves, said leaves having coaxial apertures sized to receive said container, the diameters of said apertures being less than the diameter of said rib, to support the container with said rib positioned between said leaves.

15. Apparatus in accordance with claim 14 wherein said opposed leaves position said container above and in heat transfer contact with said heater plate, and wherein said pressing means comprises weights on said opposed leaves to firmly press the container against said heater plate.

16. Apparatus in accordance with claim 15 wherein said weights have apertures which are coaxial with said apertures of said leaves.

17. Apparatus in accordance with claim 14 wherein said pressing means comprises a ramp attached to said heater and a bracket attached to said heater in opposed relation to said ramp, said opposed leaves being received between said bracket and said ramp under clamping pressure to hold said container in heat transfer contact with said heater plate.

18. Apparatus in accordance with claim 13 further comprising a pivot post on said heater and a cooperating aperture on said holder means, for permitting rotating movement of said holder means toward and away from a full heating position wherein said container is positioned entirely over said heater plate.

* * * * *

UNITED STATES PATENT AND TRADEMARK OFFICE
CERTIFICATE OF CORRECTION

PATENT NO. : 5,015,181
DATED : May 14, 1991
INVENTOR(S) : Dale B. Parask

It is certified that error appears in the above—identified patent and that said Letters Patent is hereby corrected as shown below:

Column 4, line 20:

Change the dependency from "claim 2" to read --- claim 3 ---.

Signed and Sealed this

Thirteenth Day of October, 1992

*Attest:*

DOUGLAS B. COMER

*Attesting Officer*     *Acting Commissioner of Patents and Trademarks*